US00PP17726P2

(12) United States Plant Patent
Sakazaki

(10) Patent No.: US PP17,726 P2
(45) Date of Patent: May 15, 2007

(54) *PETUNIA* PLANT NAMED 'USTUNI7501'

(50) Latin Name: *Petunia×hybrida*
Varietal Denomination: USTUNI7501

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 11/273,531

(22) Filed: Nov. 14, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Anne Marie Grunberg
*Assistant Examiner*—Georgia Helmer
(74) *Attorney, Agent, or Firm*—C. A. Whealy

(57) ABSTRACT

A new and distinct cultivar of *Petunia* plant named 'USTUNI7501', characterized by its low spreading to cascading plant habit; freely branching and vigorous growth habit; numerous single flowers that are soft pink in color; and good garden performance.

1 Drawing Sheet

Botanical designation: *Petunia×hybrida.*
Cultivar denomination: 'USTUNI7501'.

BACKGROUND OF THE INVENTION

The present Invention relates to a new and distinct cultivar of *Petunia* plant, botanically known as *Petunia×hybrida,* and hereinafter referred to by the cultivar name USTUNI7501.

The new *Petunia* is a product of a planned breeding program conducted by the Inventor in Hikone, Shiga, Japan. The objective of the breeding program is to create new disease-resistant and heat-tolerant *Petunias* with semi-upright plant habit and attractive flower colors.

The new *Petunia* originated from a cross-pollination made by the Inventor on Apr. 26, 2001 of two unnamed proprietary selections of *Petunia×hybrida,* not patented. The new *Petunia* was selected as a single plant from the resulting progeny on Jun. 18, 2002 in Gensingen, Germany, on the basis of its plant habit and attractive flower coloration.

Asexual reproduction of the new cultivar by terminal vegetative cuttings since Jun. 18, 2002, in Gensingen, Germany has shown that the unique features of this new *Petunia* are stable and reproduced true to type in successive generations.

SUMMARY OF THE INVENTION

Plants of the cultivar USTUNI7501 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USTUNI7501'. These characteristics in combination distinguish 'USTUNI7501' as a new and distinct cultivar:

1. Low spreading to cascading plant habit.
2. Freely branching and vigorous growth habit.
3. Numerous single flowers that are soft pink in color.
4. Good garden performance.

In side-by-side comparisons conducted in Hikone, Shiga, Japan, plants of the new *Petunia* differed from plants of the female parent selection in the following characteristics:

1. Plants of the new *Petunia* were more creeping than and not as upright as plants of the female parent selection.
2. Plants of the new *Petunia* were more vigorous than plants of the female parent selection.

In side-by-side comparisons conducted in Hikone, Shiga, Japan, plants of the new *Petunia* differed primarily from plants of the male parent selection in time to flower as plants of the new *Petunia* flowered earlier than plants of the male parent selection.

Plants of the new *Petunia* can be compared to plants of the cultivar Dancasoft, disclosed in U.S. Plant Pat. No. 13,383. In side-by-side comparisons conducted in Gensingen, Germany, plants of the new *Petunia* differed from plants of the cultivar Dancasoft in the following characteristics:

1. Plants of the new *Petunia* were more freely branching than plants of the cultivar Dancasoft.
2. Plants of the new *Petunia* had smaller flowers than plants of the cultivar Dancasoft.
3. Plants of the new *Petunia* were more rain tolerant than plants of the cultivar Dancasoft.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the bottom of the sheet comprises a side perspective view of a typical plant of 'USTUNI7501' grown in a container.

The photograph at the top of the sheet is a close-up view of typical flowers of 'USTUNI7501'.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers were used for the aforementioned photographs and following description. Plants were about three months from planting rooted cuttings. Plants were grown under conditions which closely approximate commercial production conditions during the spring in and outdoor nursery in Bonsall, Calif. During the production of the plants, day temperatures ranged from 13° C. to 35° C. and night temperatures ranged from 4° C. to 21° C.

Botanical classification: *Petunia×hybrida* cultivar USTUNI7501.

Parentage:

*Female parent.*—Unnamed selection of *Petunia×hybrida,* not patented.

*Male parent.*—Unnamed selection of *Petunia×hybrida,* not patented.

Propagation:

*Type cutting.*—Terminal vegetative cuttings.

*Time to initiate roots, summer and winter.*—About 15 days at 20° C. to 22° C.

*Time to develop roots, summer and winter.*—About 20 days at 18° C. to 20° C.

*Root description.*—Fine; white, close to 155D, in color.

*Rooting habit.*—Freely branching.

Plant description:

*Form/habit.*—Annual flowering plant; indeterminate; initially upright, then low spreading and cascading; uniformly mounded plant form. Freely branching habit with about eight to ten lateral branches and numerous secondary and tertiary lateral branches per plant. Pinching enhances development of lateral branches. Vigorous growth habit.

*Usage.*—Appropriate for hanging baskets, window boxes, patio containers and landscape applications.

*Plant height.*—About 21 cm.

*Plant diameter* (*area of spread*).—About 52 cm.

*Lateral branches.*—Length: About 25 cm. Diameter: About 3.5 mm. Internode length: About 1.7 cm. Texture: Pubescent; viscid. Color: 145A.

*Foliage description.*—Arrangement: Alternate before flowering; opposite after flowers develop; simple. Length: About 3.3 cm. Width: About 1.7 cm. Shape: Elliptic. Apex: Acute. Base: Attenuate. Margin: Entire. Texture, upper and lower surfaces: Pubescent; viscid. Venation pattern: Pinnate, arcuate. Color: Developing and fully expanded leaves, upper surface: 146A. Developing and fully expanded leaves, lower surface: 146B. Venation, upper surface: 146C. Venation, lower surface: 146D. Petiole length: About 5 mm. Petiole diameter: About 2.5 mm. Petiole texture, upper and lower surfaces: Pubescent. Petiole color, upper surface: 146C. Petiole color, lower surface: 146D.

Flower description:

*Flower type and habit.*—Single salverform flowers; flowers face mostly upward or outward; axillary. Freely flowering habit, about eleven flower buds and open flowers per lateral branch.

*Natural flowering season.*—Long day responsive; long flowering period, spring until frost in the autumn; flowering continuous during this period. Plants begin flowering about four to six weeks after planting rooted cuttings. Flowers persistent.

*Flower longevity on the plant.*—About five to seven days.

*Fragrance.*—Strong, sweet floral.

*Flower size.*—Diameter: About 5 cm. Depth (height): About 3.8 cm. Tube length: About 2.7 cm. Throat diameter, distal end: About 1.1 cm. Tube diameter, proximal end: About 4 mm.

*Flower buds.*—Length: About 3.7 cm. Diameter: About 6 mm. Shape: Elongated obovate. Color: 75D.

*Petals.*—Quantity/arrangement: About five petals fused in a single whorl, funnelform. Length from throat: About 2.2 cm. Width: About 2.4 cm. Shape: Roughly fan-shaped to obovate. Apex: Acute with shallow central points. Margin: Entire. Texture, upper surface: Smooth, glabrous. Texture, lower surface: Petal lobes, smooth, glabrous; tube, pubescent. Color: When opening, upper surface: 70C to 70D. When opening, lower surface: 69B. Fully opened, upper surface: 75B; venation, 75B; color becoming closer to 62D with development. Fully opened, lower surface: 69B to 69C; venation, 145B. Flower throat (inside): 157C; venation, 147D. Flower tube (outside): 155B; venation, 145B.

*Sepals.*—Arrangement/appearance: Single whorl of five sepals fused at base, star-shaped. Length: About 1.3 cm. Width: About 3 mm. Shape: Lanceolate. Apex: Rounded. Margin: Entire. Texture, upper and lower surfaces: Pubescent. Color, upper and lower surfaces: 146A.

*Peduncles.*—Length: About 3.4 cm. Width: About 1 mm. Angle: About 45° to 60° from the stem. Strength: Strong. Texture: Pubescent. Color: 146C.

*Reproductive organs.*—Stamens: Quantity per flower: Five. Anther shape: Oval. Anther size: About 1 mm by 2 mm. Anther color: 158C. Pollen amount: Moderate. Pollen color: 158B. Pistils: Quantity per flower: One. Pistil length: About 1.8 cm. Style length: About 1.6 cm. Style color: 145C. Stigma shape: Rounded; anvil-shaped. Stigma color: 146A. Ovary color: 145A.

*Seed/fruit.*—Seed and/or fruit production has not been observed.

Disease/pest resistance: Plants of the new *Petunia* have not been noted to be resistant to pathogens or pests common to *Petunia.*

Garden performance: Plants of the new *Petunia* have been observed to have good garden performance. Plants of the new *Petunia* have been noted to tolerate temperatures from 0° C. to 38° C. and have excellent tolerance to rain and wind.

It is claimed:

1. A new and distinct cultivar of *Petunia* plant named 'USTUNI7501', as illustrated and described.

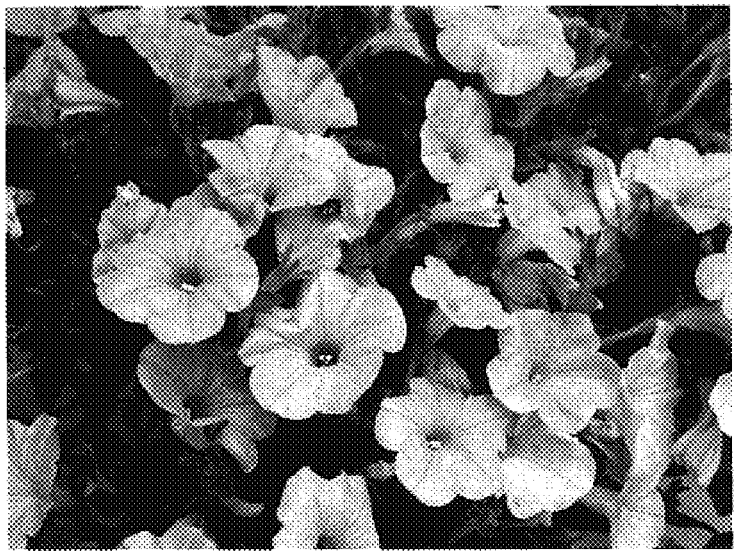
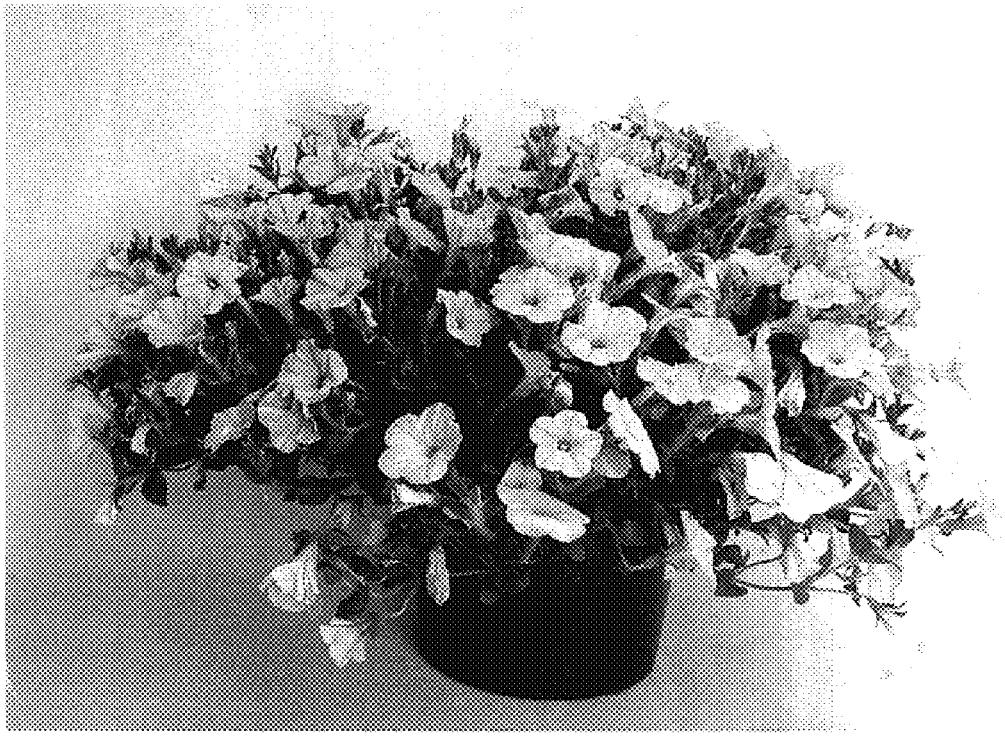

* * * * *